US012618083B2

(12) United States Patent
Jia et al.

(10) Patent No.: US 12,618,083 B2
(45) Date of Patent: May 5, 2026

(54) RECOMBINANT ADENOVIRUS EXPRESSING AFRICAN SWINE FEVER VIRUS EP153R-EP402R PROTEIN AND CONSTRUCTION METHOD THEREOF

(71) Applicant: Institute of Animal Sciences of Chinese Academy of Agricultural Sciences, Beijing (CN)

(72) Inventors: Hong Jia, Beijing (CN); Hongfei Zhu, Beijing (CN); Xiaoyu Guo, Beijing (CN); Weifeng Yuan, Beijing (CN); Shuai Cui, Beijing (CN); Yang Wang, Beijing (CN); Ting Xin, Beijing (CN)

(73) Assignee: Institute of Animal Sciences of Chinese Academy of Agricultural Sciences, Beijing (CN)

( * ) Notice: Subject to any disclaimer, the term of this patent is extended or adjusted under 35 U.S.C. 154(b) by 759 days.

(21) Appl. No.: 18/057,765

(22) Filed: Nov. 22, 2022

(65) Prior Publication Data

US 2023/0167462 A1      Jun. 1, 2023

(30) Foreign Application Priority Data

Nov. 26, 2021     (CN) .......................... 202111425085.4

(51) Int. Cl.
*C12N 15/86*        (2006.01)
*C07K 14/01*        (2006.01)

(52) U.S. Cl.
CPC .............. *C12N 15/86* (2013.01); *C07K 14/01* (2013.01); *C12N 2710/12041* (2013.01)

(58) Field of Classification Search
None
See application file for complete search history.

(56) References Cited

FOREIGN PATENT DOCUMENTS

CN          112080521 A  * 12/2020  ............. C12N 15/85

* cited by examiner

*Primary Examiner* — Tracy Vivlemore
*Assistant Examiner* — Hanna Marie Thueson

(57)          ABSTRACT

The present disclosure provides a recombinant adenovirus for expressing African swine fever virus (ASFV) EP153R-EP402R protein and a construction method thereof, and belongs to the technical field of genetic engineering. In the present disclosure, a recombinant adenovirus vector pAD-CMV-EGFP-EP153R-EP402R is obtained through a series of intermediate processes using a recombinant adenovirus shuttle vector pENTRE-EGFP-TOPO; the recombinant adenovirus vector is linearized to transfect AD293 cells, a recombinant virus is screened according to cytopathy formed by adenovirus infection, an adenovirus packaging process is achieved, and the recombinant adenovirus for expressing ASFV EP153R-EP402R protein is obtained, laying a foundation for the construction of a recombinant adenovirus vaccine for expressing the ASFV EP153R-EP402R protein.

5 Claims, 3 Drawing Sheets

Specification includes a Sequence Listing.

RECOMBINANT ADENOVIRUS EXPRESSING AFRICAN SWINE FEVER VIRUS EP153R-EP402R PROTEIN AND CONSTRUCTION METHOD THEREOF

CROSS REFERENCE TO RELATED APPLICATION

This patent application claims the benefit and priority of Chinese Patent Application No. 202111425085.4, filed on Nov. 26, 2021, the disclosure of which is incorporated by reference herein in its entirety as part of the present application.

REFERENCE TO SEQUENCE LISTING

A computer readable XML file entitled "GWP20220700545", that was created on Nov. 10, 2022, with a file size of about 3,612 bytes, contains the sequence listing for this application, has been filed with this application, and is hereby incorporated by reference in its entirety.

TECHNICAL FIELD

The present disclosure relates to the technical field of genetic engineering, in particular to a recombinant adenovirus expressing African swine fever virus (ASFV) EP153R-EP402R protein and a construction method thereof.

BACKGROUND ART

African swine fever (ASF) is an acute, severe and highly contagious infectious disease caused by African swine fever virus (ASFV). Clinical manifestations include fever, skin cyanosis, obvious bleeding in lymph nodes, kidneys, and gastrointestinal mucosa.

ASFV is the sole member of the genus *Asfivirus* within the family Asfarviridae, and the only DNA arbovirus at present. It is generally considered to have only one serotype. Internationally, ASFV is divided into 24 genotypes according to a 478 bp nucleic acid sequence at the terminal of ASFV B646L gene, most of which belong to genotype II in China. ASFV can be transmitted by domestic pigs, wild boars and soft ticks, and mainly attacks swine monocytes and macrophages. The virion has a diameter of 175-215 nm. It is icosahedral and enveloped, structurally comprising, from the inside out, a nucleoid, a nucleocapsid, an inner envelope, a capsid, and external envelope. The genome is double-stranded linear DNA with a size of 170-193 kb and 150-167 open reading frames, encoding more than 50 structural proteins and more than 100 non-structural proteins. The main substances involved in the structural composition of virions include structural proteins, gene transcription and RNA modification enzymes. As the main components of virions, structural proteins play important roles in ASFV adsorption, invasion and replication and other infectious processes. The encoding proteins mainly include p72, p49, p30, p54, EP153R, CD2v, and the like. The EP153R protein is encoded by the EP153R gene located in the ASFV EcoRI E9 genome fragment, is approximately 18 kDa in size, and is transcribed at the early and late stages of viral infection. The insertion of the marker gene LacZ into EP153R does not change the growth rate of the virus in vitro and the sensitivity and drug resistance of the virus, but it eliminates the hemosorption induced by ASFV-infected cells. EP153R stabilizes the interaction between EP402R and other ligands and participates in mediating apoptosis. CD2v protein is named because it is similar to the adhesion molecule CD2 on the surface of T cells. It is encoded by the EP402R gene and has a size of approximately 45.3 kDa. It is embedded in the outer surface of the viral envelope and is a glycoprotein composed of a signal peptide, a transmembrane domain, and a plasmic tail domain containing 147 amino acids. The CD2v protein enables virions to attach to erythrocytes and acts as an essential protein for erythrocytes to bind to infected cells and extracellular virions. The expression of CD2v is associated with the spread of ASFV among domestic pigs, which can disrupt the function of lymphocytes. At present, there is no recombinant adenovirus against EP153R-EP402R and a feasible method for preparing the recombinant adenovirus.

SUMMARY

An objective of the present disclosure is to provide a recombinant adenovirus expressing ASFV EP153R-EP402R protein and a construction method thereof, so as to solve the above-mentioned problems existing in the prior art and lay a technical foundation for the study of ASF candidate vaccines.

To achieve the above objective, the present disclosure provides the following solutions:

The present disclosure provides a recombinant adenovirus vector expressing ASFV EP153R-EP402R protein, where based on a pAD-CMV-3×FLAG adenovirus vector, EP153R-EP402R gene is introduced to construct a recombinant adenovirus vector pAD-CMV-EGFP-EP153R-EP402R; the EP153R-EP402R gene has a nucleotide sequence shown in SEQ ID NO: 1.

The present disclosure further provides a construction method of the foregoing recombinant adenovirus vector expressing ASFV EP153R-EP402R protein, including the following steps:

step 1, synthesizing an EP153R-EP402R gene, and adding four bases, CACC, before a start codon of the EP153R-EP402R gene;

step 2, conducting TOPO cloning on the EP153R-EP402R gene obtained in step 1 and a pENTRE-EGFP-TOPO vector to obtain pENTR-EGFP-ASFV-EP153R-EP402R; and step 3, recombining the pENTR-EGFP-ASFV-EP153R-EP402R obtained in step 2 on an adenovirus backbone vector pAD-CMV-3×FLAG through LR recombination reaction to obtain the recombinant adenovirus vector pAD-CMV-EGFP-EP153R-EP402R.

The present disclosure further provides a recombinant adenovirus packaging method; the foregoing recombinant adenovirus vector pAD-CMV-EGFP-EP153R-EP402R is single-digested with PacI, and a linearized plasmid is used for transfection; 293t cells are transfected to achieve recombinant adenovirus packaging.

Further, the following steps may be included:

step 1, single-digesting the recombinant adenovirus vector pAD-CMV-EGFP-EP153R-EP402R with a restriction endonuclease PacI, and transfecting the linearized plasmid into AD293 cells;

step 2, after transfection until cell detachment, rounding and space enlargement, collecting cells and a supernatant, namely P1 recombinant adenovirus; and step 3, infecting 293t cells with the P1 recombinant adenovirus, and observing cell status.

Further, a transfection reagent for transfecting the AD293 cells may be a transfection reagent of jetPRIME kit.

Further, in step 2, the cells and the supernatant are collected, freeze-thawed three times at −80° C., and centrifuged at 12,000×g for 10 min to collect a supernatant.

The present disclosure further provides a recombinant adenovirus prepared by the foregoing recombinant adenovirus packaging method, including the foregoing recombinant adenovirus vaccine.

The present disclosure provides the following technical effects:

In the present disclosure, a recombinant adenovirus vector pAD-CMV-EGFP-EP153R-EP402R is obtained through a series of intermediate processes using a recombinant adenovirus shuttle vector pENTRE-EGFP-TOPO; the recombinant adenovirus vector is linearized to transfect AD293 cells, a recombinant virus is screened according to cytopathy formed by adenovirus infection, an adenovirus packaging process is achieved, and the recombinant adenovirus for expressing ASFV EP153R-EP402R protein is obtained, laying a foundation for the construction of a recombinant adenovirus vaccine for expressing the ASFV EP153R-EP402R protein.

BRIEF DESCRIPTION OF THE DRAWINGS

In order to more clearly illustrate the examples of the present disclosure or the technical solutions in the prior art, the accompanying drawings required in the examples will be briefly introduced below. Obviously, the accompanying drawings in the following description are only some examples of the present disclosure. Other drawings can be obtained by those of ordinary skill in the art without creative efforts based on these drawings.

DETAILED DESCRIPTION OF THE EMBODIMENTS

A plurality of exemplary embodiments of the present disclosure will now be described in detail. The detailed description should not be construed as a limitation of the present disclosure, but rather as a more detailed description of certain aspects, features, and embodiments of the present disclosure.

It should be appreciated that the terms described in the present disclosure are only intended to describe specific embodiments and are not intended to limit the present disclosure. Additionally, for numerical ranges in the present disclosure, it should be appreciated that each intermediate value between the upper and lower limits of the range is also specifically disclosed. Each smaller range between any stated value or intermediate value in a stated range and any other stated value or intermediate value in that stated range is also included within the present disclosure. The upper and lower limits of these smaller ranges may independently be included or excluded in the range.

Unless otherwise defined, all technical and scientific terms used herein have the same meanings as commonly understood by one of ordinary skill in the art to which this present disclosure relates. Although only the preferred methods and materials are described herein, any methods and materials similar or equivalent to those described herein can also be used in the practice or testing of the present disclosure. All documents mentioned in this specification are incorporated by reference for the purpose of disclosing and describing the methods and/or materials in connection with which the documents are referred. In the event of conflict with any incorporated document, the content of this specification shall prevail.

It will be apparent to those skilled in the art that a plurality of modifications and variations can be made in the specific embodiments of the present disclosure without departing from the scope or spirit of the present disclosure. Other embodiments derived from the description of the present disclosure will be apparent to those skilled in the art. The specification and examples of the present disclosure are merely exemplary.

As used herein, "comprising," "including," "having," "containing," and the like, are all open-ended terms, meaning including but not limited to.

In the following examples, the experimental methods that do not indicate specific conditions, usually according to conventional conditions, are conducted as described in the *Short Protocols in Molecular Biology* (F. M. Ausubel, R. E. Kingston, J. G. Seidman, et al. Ma Xuejun, Shu Yuelong (translators). Beijing: Science Press, 2004).

Figure 2:
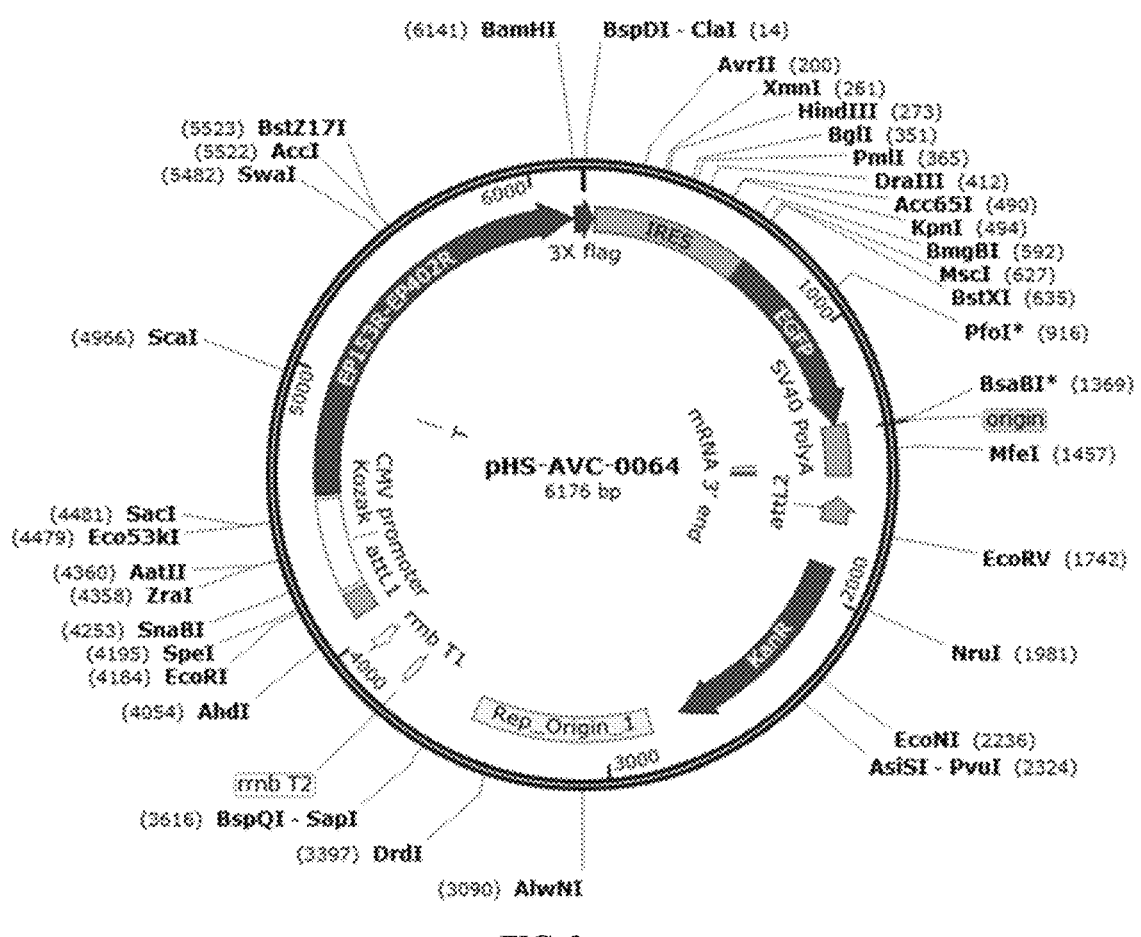
FIG. 2 illustrates the structure of a transition vector recombinant plasmid pENTR-EGFP-ASFV-EP153R-EP402R.

The present disclosure provides a construction method of a recombinant adenovirus expressing ASFV EP153R-EP402R protein, including the following steps:

(1) The EP153R-EP402R gene (GeneID: 59226985+59226986) included on the NCBI website was queried, a gene fragment was artificially synthesized, four bases, CACC, were added before the start codon, and the gene fragment was ligated to the transition vector pENTRE-EGFP-TOPO to obtain a transition vector recombinant plasmid pENTR-EGFP-ASFV-EP153R-EP402R, as shown in FIG. 2.

Figure 3:
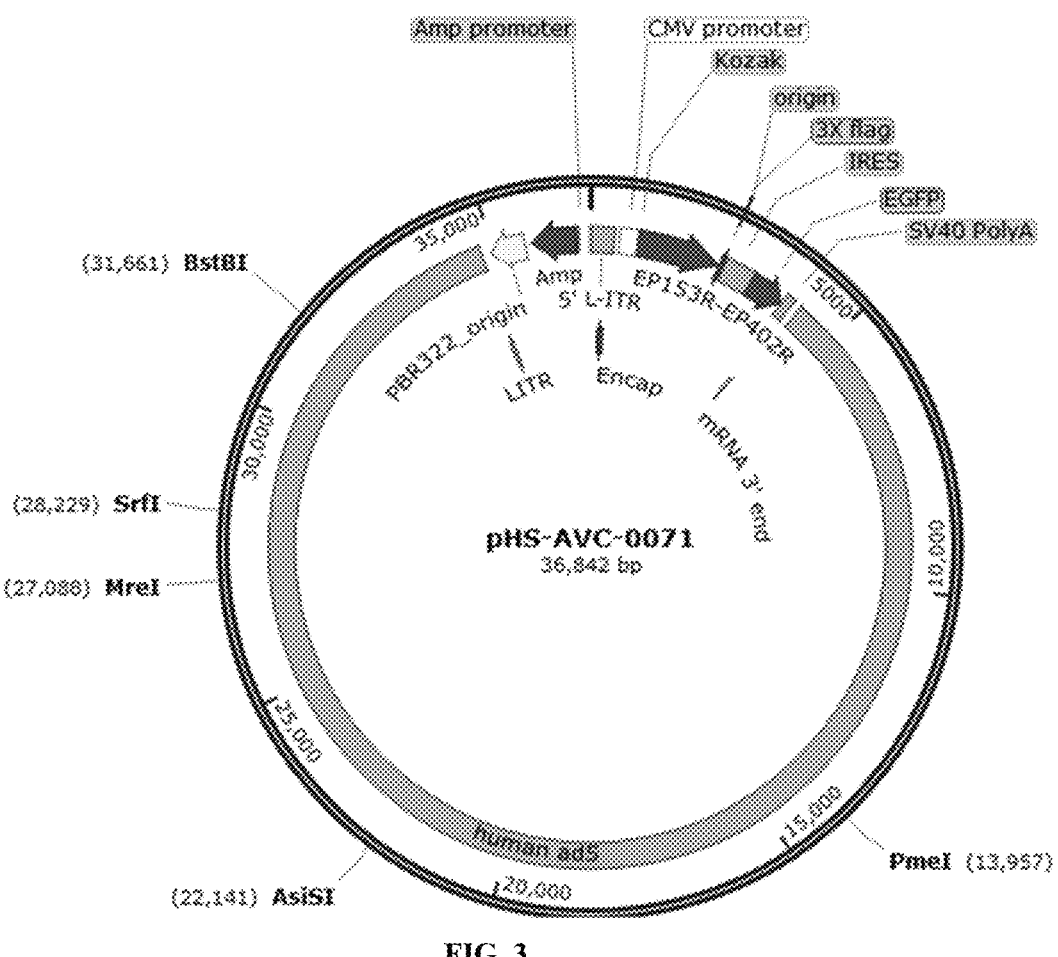
FIG. 3 illustrates the plasmid structure of a recombinant adenovirus vector pAD-CMV-EGFP-EP153R-EP402R.

(2) The transition vector recombinant plasmid pENTR-EGFP-ASFV-EP153R-EP402R obtained in step (1) was recombined with an adenovirus backbone vector pAD-CMV-3×FLAG by LR recombination reaction, and transformed to obtain a recombinant adenovirus vector pAD-CMV-EGFP-EP153R-EP402R, as shown in FIG. 3.

(3) The recombinant adenovirus vector pAD-CMV-EGFP-EP153R-EP402R was digested with Pad and linearly transfected into AD293 cells to obtain recombinant adenovirus.

Synthesis of EP153R-EP402R gene:

The EP153R-EP402R gene (GeneID: 59226985+59226986) included on the NCBI website was queried, a gene fragment was artificially synthesized, and four bases, CACC, were added before the start codon. The final sequence is shown in SEQ ID NO: 1.

```
SEQ ID NO: 1:
ATGTTTTCTAACAAAAAGTACATCGGTCTTATCAA

TAAGAAGGAGGGTTTGAAAAAAAAAATAGATGATT

ATAGTATATTAATAATTGGAATATTAATTGGAACT

AACATCTTAAGCCTTATTTATAAATATAATAGGAGA

GATTAATAAACCAATATGTTACCAAAATGATGATA

AGATATTTTATTGCCCTAAAGATTGGGTTGGATAT

AATAATGTTTGTTATTATTTTGGCAATGAAGAAAA

AAATTATAATAATGCAAGTAATTATTGTAAGCAAT
```

-continued

```
TAAATAGTACGCTTACTAATAATAATACTATTTTA

GTAAATCTTACTAAAACATTAAATCTTACTAAAAC

ATATAATCACGAATCTAATTATTGGGTTAATTATT

CTTTAATTAAAAATGAGTCAGTACTATTACGTGAT

AGTGGATATTACAAAAAACAAAAACATGTAAGTTT

ATTATATATTTGTAGTAAAGGAGGCGGAAGCGGCG

GTGGAGGATCAATGATAATACTTATTTTTTTAATA

TTTTCTAACATAGTTTTAAGTATTGATTATTGGGT

TAGTTTTAATAAAACAATAATTTTAGATAGTAATA

TTACTAATGATAATAATGATATAAATGGAGTATCA

TGGAATTTTTTTAATAATTCTTTTAATACACTAGC

TACATGTGGAAAAGCAGGTAACTTTTGTGAATGTT

CTAATTATAGTACATCAATATATAATATAACAAAT

AATTGTAGCTTAACTATTTTTCCTCATAATGATGT

ATTTGATACAACATATCAAGTAGTATGGAATCAAA

TAATTAATTATACAATAAAATTATTAACACCTGCT

ACTCCCCCAAATATCACATATAATTGTACTAATTT

TTTAATAACATGTAAAAAAAATAATGGAACAAACA

CTAATATATATTTAAATATAAATGATACTTTTGTT

AAATATACTAATGAAAGTATACTTGAATATAACTG

GAATAATAGTAACATTAACAATTTTACAGCTACAT

GTATAATTAATAATACAATTAGTACATCTAATGAA

ACAACACTTATAAATTGTACTTATTTAACATTGTC

ATCTAACTATTTTTATACTTTTTTTAAATTATATT

ATATTCCATTAAGCATCATAATTGGGATAACAATA

AGTATTCTTCTTATATCCATCATAACTTTTTTATC

TTTACGAAAAGAAAAAAACATGTTGAAGAAATAG

AAAGTCCACCACCTGAATCTAATGAAGAAGAACAA

TGTCAGCATGATGACACCACTTCCATACATGAACC

ATCTCCCAGAGAACCATTACTTCCTAAGCCTTACA

GTCGTTATCAGTATAATACACCTATTTACTACATG

CGTCCCTCAACACAACCACTCAACCCATTTCCCTT

ACCTAAACCGTGTCCTCCACCCAAACCATGTCCGC

CACCCAAACCATGTCCTCCACCTAAACCATGTCCT

TCAGCTGAATCCTATTCTCCACCCAAACCACTACC

TAGTATCCCGCTACTACCCAATATCCCGCCATTAT

CTACCCAAAATATTTCGCTTATTCACGTAGATAGA

ATTATT
```

Construction of recombinant adenovirus vector pAD-CMV-EGFP-EP153R-EP402R:

(1) The constructed transition vector recombinant plasmid pENTR-EGFP-ASFV-EP153R-EP402R was recombined with the adenovirus backbone vector pAD-CMV-3×FLAG by LR recombination reaction. The LR recombination reaction system is shown in Table 1.

Table 1 LR recombination reaction system

| Component | Volume |
|---|---|
| pENTR-EGFP-ASFV- EP153R-EP402R | 1 μL |
| pAD-CMV-3 × FLAG | 2 μL |
| 5 × LR Clonase ™ reaction buffer | 4 μL |
| TE Buffer, pH 8.0 | 9 μL |

4 μL of Vortex×LR Clonase™ enzyme MiX was added to the above components, and vortexed to mix; the mixture was incubated at 25° C. for 1 h; 2 μL of 2 μg/μL proteinase K solution was added, followed by incubation at 37° C. for 10 min.

(2) *Escherichia coli* DH5α competent cells were screened on ampicillin-resistant LB plates, and single clones were picked for PCR identification to obtain recombinant adenovirus vector pAD-CMV-EGFP-EP153R-EP402R.

Recombinant adenovirus packaging:

(1) AD293 cell plating: 2 mL/well cell suspension was pipetted into a 6-well plate, and placed in a 37° C., 5% $CO_2$ incubator to continue culturing; when the 293T cells in the 6-well plate were cultured to a confluence of 70%-80%, they were transfected;

(2) Plasmid preparation: 2 μg of linearized pAD-CMV-EGFP-EP153R-EP402R was added to 200 μL of jetPRIME® buffer, vortexed to mix well for 10 s, and then centrifuged to the bottom of the tube transiently; 4 μL of jetPRIME® transfection reagent was added, vortexed to mix well for 1 s, centrifuged transiently, and allowed to stand at room temperature for 10 min; the mixture was added dropwise to the medium, shaken gently, and incubated at 37° C.

Figure 1:
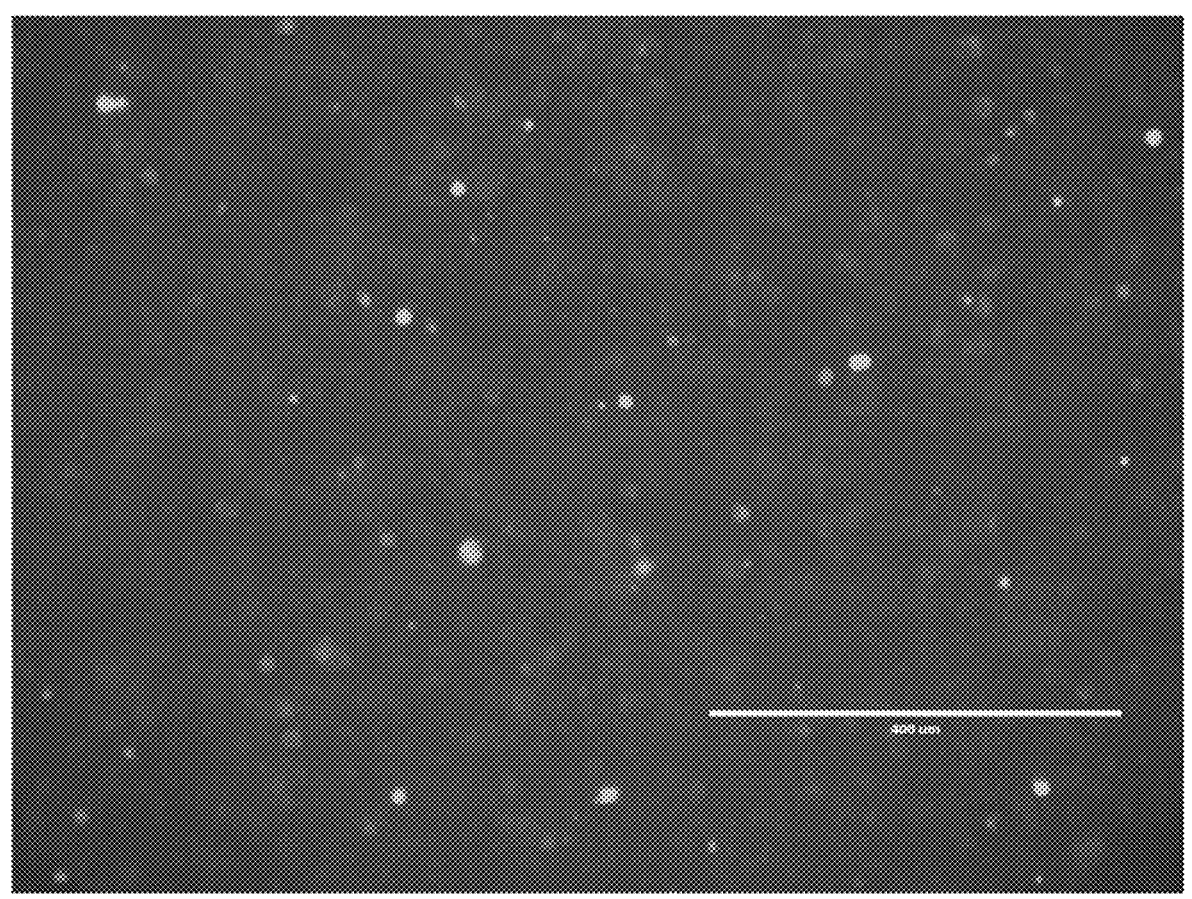
FIG. 1 illustrates the packaging of a recombinant adenovirus vector pAD-CMV-EGFP-EP153R-EP402R.

(3) Fluorescent expression was observed at 72 h; the state of AD293 cells and the virus plating efficiency were observed at about 7 days; when cell detachment, rounding and space enlargement were observed (FIG. 1), the supernatant and cells were all collected and freeze-thawed at −80° C. three times, and centrifuged at 12,000×g for 10 min to collect a supernatant.

(4) The collected recombinant adenovirus was inoculated into the 293T cells that had grown to a monolayer in a T25 flask. When approximately 50% of the cells were detached in 5-7 days, the supernatant and cells were collected and freeze-thawed at −80° C. three times, and centrifuged at 12,000×g for 10 min to collect a supernatant.

(5) The T25 flask was infected repeatedly, and viruses were collected.

(6) The recombinant adenovirus was concentrated and purified.

Titer Determination of Recombinant Adenovirus

The recombinant adenovirus diluted $10^{-6}$-fold was inoculated into 293T cells, and the titer of the recombinant adenovirus was determined using the Adeno-×Rapid Titer Kit. A cell count was performed in a visual field with 5-50 positive cells, and the recombinant adenovirus titer was calculated. The result was $10^{10}$ PFU/mL.

Validation of Adenovirus Expression

1) Cell preparation: 0.5 mL/well cell suspension was pipetted into a 24-well plate, and placed in a 37° C., 5% $CO_2$ incubator to continue culturing; when the 293T cells in the 24-well plate were cultured to a confluence of 80%, they were infected;

2) 50 μL of the above recombinant adenovirus supernatant was pipetted to infect the cells, and the fluorescence was observed at 72 h.

3) Western blot (WB) detection was conducted using tagged protein. The detection results showed that a specific band appeared at about 60 kD, which was consistent with the expected results. It can be seen that cells infected with successfully packaged recombinant adenovirus can express EP153R-EP402R protein.

The above examples are only intended to describe the preferred implementations of the present disclosure, but not to limit the scope of the present disclosure. Various alterations and improvements made by those of ordinary skill in the art without departing from the design spirit of the present disclosure shall fall within the scope of the appended claims of the present disclosure.

EP402R; the EP153R-EP402R gene has a nucleotide sequence shown in SEQ ID NO: 1.

2. A construction method of the recombinant adenovirus vector expressing ASFV EP153R-EP402R protein according to claim 1, comprising the following steps:

step 1, synthesizing an EP153R-EP402R gene, and adding four bases, CACC, before a start codon of the EP 153R-EP402R gene;

step 2, conducting TOPO cloning on the EP153R-EP402R gene obtained in step 1 and a pENTRE-EGFP-TOPO vector to obtain pENTR-EGFP-ASFV-EP153R-EP402R; and step 3, recombining the pENTR-EGFP-ASFV-EP153R-EP402R obtained in step 2 on an adenovirus backbone vector pAD-CMV-3×FLAG through LR recombination reaction to obtain the recombinant adenovirus vector pAD-CMV-EGFP-EP153R-EP402R.

3. A recombinant adenovirus packaging method, wherein the recombinant adenovirus vector pAD-CMV-EGFP-EP153R-EP402R according to claim 1 is single-digested with PacI, and a linearized plasmid is used for transfection; 293t cells are transfected to achieve recombinant adenovirus packaging.

---

---

We claim:

1. A recombinant adenovirus vector expressing African swine fever virus (ASFV) EP153R-EP402R protein, wherein based on a pAD-CMV-3×FLAG adenovirus vector, EP153R-EP402R gene is introduced to construct a recombinant adenovirus vector pAD-CMV-EGFP-EP153R-

4. The recombinant adenovirus packaging method according to claim 3, comprising the following steps:

step 1, single-digesting the recombinant adenovirus vector pAD-CMV-EGFP-EP153R-EP402R with a restriction endonuclease PacI, and transfecting the linearized plasmid into AD293 cells;

step 2, after transfection until cell detachment, rounding and space enlargement, collecting cells and a supernatant, namely P1 recombinant adenovirus; and step 3, infecting 293t cells with the P1 recombinant adenovirus, and observing cell status.

5. The recombinant adenovirus packaging method according to claim 4, wherein in step 2, the cells and the supernatant are collected, freeze-thawed three times at −80° C., and centrifuged at 12,000×g for 10 min to collect a supernatant.

\* \* \* \* \*

SEQUENCE LISTING

```
Sequence total quantity: 1
SEQ ID NO: 1              moltype = DNA  length = 1581
FEATURE                  Location/Qualifiers
source                   1..1581
                         mol_type = other DNA
                         note = Nucleotide sequence of EP153R-EP402R gene
                         organism = synthetic construct
SEQUENCE: 1
atgttttcta acaaaaagta catcggtctt atcaataaga aggagggttt gaaaaaaaaa  60
atagatgatt atagtatatt aataattgga atattaattg gaactaacat cttaagcctt  120
attataaata taataggaga gattaataaa ccaatatgtt accaaaatga tgataagata  180
ttttattgcc ctaaagattg ggttggatat aataatgttt gttattattt tggcaatgaa  240
gaaaaaaatt ataataatgc aagtaattat tgtaagcaat taaatagtac gcttactaat  300
aataatacta ttttagtaaa tcttactaaa acattaaatc ttactaaaac atataatcac  360
gaatctaatt attgggttaa ttattctta attaaaaatg agtcagtact attacgtgat  420
agtggatatt acaaaaaaca aaaacatgta agtttattat atatttgtag taaaggaggc  480
ggaagcggcg gtggaggatc aatgataata cttatttttt taatattttc taacatagtt  540
ttaagtattg attattgggt tagtttttaat aaaacaataa ttttagatag taatattact  600
aatgataata atgatataaa tggagtatca tggaattttt ttaataattc ttttaataca  660
ctagctacat gtggaaaagc aggtaacttt tgtgaatgtt ctaattatag tacatcaata  720
tataatataa caaataattg tagcttaact attttttcctc ataatgatgt atttgataca  780
acatatcaag tagtatggaa tcaaataatt aattatacaa taaaattatt aacacctgct  840
actcccccaa atatcacata taattgtact aatttttaa taacatgtaa aaaaaataat  900
ggaacaaaca ctaatatata tttaaatata aatgatactt ttgttaaata tactaatgaa  960
agtatacttg aatataactg gaataatagt aacattaaca attttacagc tacatgtata  1020
attaataata caattagtac atctaatgaa acaacactta taaattgtac ttatttaaca  1080
ttgtcatcta actatttta tactttttttt aaattatatt atattccatt aagcatcata  1140
attgggataa caataagtat tcttcttata tccatcataa ctttttttatc tttacgaaaa  1200
agaaaaaaac atgttgaaga aatagaaagt ccaccacctg aatctaatga agaagaacaa  1260
tgtcagcatg atgacaccac ttccatacat gaaccatctc ccagagaacc attacttcct  1320
aagccttaca gtcgttatca gtataataca cctatttact acatgcgtcc ctcaacacaa  1380
ccactcaacc catttccctt acctaaaccg tgtcctccac ccaaaccatg tccgccaccc  1440
aaaccatgtc ctccacctaa accatgtcct tcagctgaat cctattctcc acccaaacca  1500
ctacctagta tcccgctact acccaatatc ccgccattat ctacccaaaa tatttcgctt  1560
attcacgtag atagaattat t                                          1581
```